US012558402B2

(12) United States Patent
Spragg et al.

(10) Patent No.: US 12,558,402 B2
(45) Date of Patent: Feb. 24, 2026

(54) JELLYFISH COLLAGEN USE

(71) Applicants: JELLAGEN PTY LTD, Stirling (GB); MAYO FOUNDATION FOR MEDICAL EDUCATION AND RESEARCH, Rochester, MN (US)

(72) Inventors: Andrew Mearns Spragg, Stirling (GB); Dale Ekbom, Rochester, MN (US); Serban San-Marina, Rochester, MN (US)

(73) Assignees: JELLAGEN PTY LTD, Sterling (GB); MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 588 days.

(21) Appl. No.: 18/010,762

(22) PCT Filed: Jun. 15, 2021

(86) PCT No.: PCT/GB2021/051491
§ 371 (c)(1),
(2) Date: Dec. 15, 2022

(87) PCT Pub. No.: WO2021/255432
PCT Pub. Date: Dec. 23, 2021

(65) Prior Publication Data
US 2023/0218724 A1 Jul. 13, 2023

Related U.S. Application Data

(60) Provisional application No. 63/039,716, filed on Jun. 16, 2020.

(30) Foreign Application Priority Data

Jul. 9, 2020 (GB) ..................................... 2010544

(51) Int. Cl.
A61K 38/39 (2006.01)
A61K 35/28 (2015.01)
A61P 11/04 (2006.01)

(52) U.S. Cl.
CPC .............. *A61K 38/39* (2013.01); *A61K 35/28* (2013.01); *A61P 11/04* (2018.01)

(58) Field of Classification Search
CPC ...... A61K 38/39; A61K 35/28; A61K 35/614; A61K 38/1767; A61P 11/04; A61P 43/00
See application file for complete search history.

(56) References Cited

U.S. PATENT DOCUMENTS

| | | | |
|---|---|---|---|
| 8,658,711 B2 * | 2/2014 | Shreiber ................... | C08H 1/06 |
| | | | 536/55.1 |
| 2008/0260794 A1 * | 10/2008 | Lauritzen ................ | A61L 15/32 |
| | | | 424/548 |
| 2016/0052962 A1 | 2/2016 | Lim et al. | |
| 2017/0360986 A1 * | 12/2017 | Paten ................. | A61K 38/4886 |

FOREIGN PATENT DOCUMENTS

WO WO 2018/220396 A1 12/2018

OTHER PUBLICATIONS

Hoffman H et al. Laryngeal Collagen Injection as an Adjunct to Medialization Laryngoplasty. 2002. The Laryngoscope. p. 1407-1413. (Year: 2002).*
Li Y et al. Adipose-derived mesenchymal stem cells accelerate nerve regeneration and functional recovery in a rat model of recurrent laryngeal nerve injury. 2017. Neural Regeneration Research. vol. 12, Issue 9. p. 1544-1550. (Year: 2017).*
Nicolas FL et al. Denatured Thiolated Collagen. 1997. Biomaterials. 807-813. (Year: 1997).*
Bowen, A. J. et al., "Larynx proteomics after jellyfish collagen IL: Increased ECM/collagen and suppressed inflammation," *Laryngoscope Investigative Otolaryngology*, 7 (2022): 1513-1520.
Eppley, B. L. et al.,"Injectable Soft-Tissue Fillers: Clinical Overview," *Plastic and Reconstructive Surgery*, 118.4 (2006): 98e-106e.
Gulka, C. P. et al., "A Novel Silk-Based Vocal Fold Augmentation Material: 6-Month Evaluation in a Canine Model," *The Laryngoscope*, 129 (2019): 1856-1862.
Jellagen: Jellyfish Collagen Biomaterials, Overview Presentation, 2016: 1-14.
Kimura, M. et al., "Collagen Injection as a Supplement to Arytenoid Adduction for Vocal Fold Paralysis,", *Annals of Otology, Rhinology & Laryngology*, 117.6 (2008): 430-436.
Kimura, M. et al., "Clinical experience with collagen injection of the vocal fold: A study of 155 patients," *Auris Nasus Larynx*, 35 (2008): 67-75.
Latify, N. et al., "A tissue-mimetic nano-fibrillar hybrid injectable hydrogel for potential soft tissue engineering applications," *Scientific Reports*, 8 (2018): 1-18.
Lehr, R., "Sixteen S-Squared Over D-Squared: A Relation for Crude Sample Size Estimates," *Statistics in Medicine*, 11 (1992): 1099-1102.
Li, L. et al., "Tissue Engineering-based Therapeutic Strategies for Vocal Fold Repair and Regeneration," *Biomaterials*, 108 (2016): 91-110.
Mallur, P. S. et al., "Vocal Fold Injection: Review of Indications, Techniques, and Materials for Augmentation," *Clinical and Experimental Otorhinolaryngology*, 3.4 (2010): 177-182.
Oldenburg, M. S. et al., "Histologic Evaluation of Micronized AlloDerm After Injection Laryngoplasty in a Rabbit Model," *The Laryngoscope*, 127 (2017): E166-E169.
Oldenburg, M. S. et al., "Preliminary Results of Tissue-Engineered Injection Laryngoplasty Material in a Rabbit Model," *The Laryngoscope*, 128 (2018): 160-167.

(Continued)

*Primary Examiner* — Paul J Holland
(74) *Attorney, Agent, or Firm* — pH IP Law

(57) ABSTRACT

The present invention relates to jellyfish collagen for use in the treatment of vocal fold paralysis.

14 Claims, 13 Drawing Sheets

(56)                    References Cited

OTHER PUBLICATIONS

Remacle, M. et al., "Treatment of vocal fold immobility by inject-able homologous collagen: short-term results," *Eur Arch Otorhinolaryngol*, 263 (2006): 205-209.

Siu, J. et al. "A Comparison of Outcomes in Interventions for Unilateral Vocal Fold Paralysis: A Systematic Review," *The Laryngoscope*, 126 (2016): 1616-1624.

Spataro, E. A. et al., "Etiology and Time to Presentation of Unilateral Vocal Fold Paralysis," *American Academy of Otolaryngology*, 151.2 (2014): 256-293.

Spiegel, J. R. et al., "The Treatment of Vocal Fold Paralysis with Injectable Collagen: Clinical Concerns," *Journal of Voice*, 1.1 (1987): 119-121.

Wen, M-H. et al., "Treatment Outcomes of Injection Laryngoplasty Using Cross-Linked Porcine Collagen and Hyaluronic Acid," *American Academy of Otolaryngology*, 149.6 (2013): 900-906.

Widdowson, J. P. et al., "In vivo comparison of jellyfish and bovine collagen sponges as prototype medical devices," *J Biomed Mater Res Part B*, 106B (2018): 1524-1533.

Voss, S. et al., "Histone Variants as Stem Cell Biomarkers for Long-Term Injection Medialization Laryngoplasty," *The Laryngoscope*, 128 (2018): E402-E408.

Zeitels, S. M. et al., "Vocal Fold Injection of Absorbable Materials: A Histologic Analysis With Clinical Ramifications," *Annals of Otology, Rhinology & Laryngology*, 128.3S (2019): 71S-81S.

Damrose, E. J., "Percutaneous Injection Laryngoplasty in the Management of Acute Vocal Fold Paralysis," *The Laryngoscope*, 120.8 (2010): 1582-1590.

* cited by examiner

| Rabbits | | Procedure | | | µL injected | Sacrifice week | µL volume | Histology | | Complications? |
|---|---|---|---|---|---|---|---|---|---|---|
| | | VFP | IL | ADSC | | | | MRI validation? | Features | |
| Group 1 | (1) | + | +/- | 10^6 | 100 | 4 | 9.34 | +/- | MA | Seroma-drained |
| | (2) | + | +/- | 10^6 | 120 | 4 | 34.5 | + | HN | N/A |
| | (3) | + | +/- | 10^6 | 120 | 4 | 37.8 | + | A, HN | N/A |
| | (4) | + | + | 10^6 | 100 | 12 | 16.8 | +/- | MA | N/A |
| | (5) | + | +/- | 10^6 | 170 | 12 | 7.10 | +/- | A | Seroma |
| | (6) | + | +/- | 10^6 | 150 | 12 | 15.3 | +/- | A, LN | N/A |
| Group 2 | (7) | + | + | N/A | 100 | 4 | 73.5 | + | HN | N/A |
| | (8) | + | + | N/A | 100 | 4 | 40.9 | + | HN | N/A |
| | (9) | + | + | N/A | 100 | 4 | 68.0 | + | HN | N/A |
| | (10) | + | +/- | N/A | 100 | 12 | 1.70 | - | A, MA | Seroma-drained |
| | (11) | + | + | N/A | 100 | 12 | 26.0 | + | HN | N/A |
| | (12) | + | + | N/A | 100 | 12 | 29.5 | + | A, HN | N/A |
| Group 3 | (13) | + | + | N/A | 100 | 4 | 29.5 | + | MD/F | N/A |
| | (14) | +/- | + | N/A | 100 | 4 | 14.9 | + | A, MD/F | Wound dehiscence |
| | (15) | + | +/- | N/A | 110 | 4 | 37.7 | + | A, MD/F | N/A |
| | (16) | + | + | N/A | 100 | 12 | 5.04 | + | MD/F | N/A |
| | (17) | - | + | N/A | 100 | 12 | 19.7 | +/- | A, MD/F | N/A |
| | (18) | + | + | N/A | 100 | 12 | 7.00 | +/- | A, MD | N/A |
| Group 4 | (19) | + | + | N/A | 100 | 4 | 44.4 | + | LN | N/A |
| | (20) | + | + | N/A | 100 | 4 | 42.9 | + | A, LN | N/A |
| | (21) | + | + | N/A | 100 | 12 | 25.2 | + | A, LN | N/A |
| | (22) | + | + | N/A | 100 | 12 | 10.4 | + | LN | Seroma-drained |
| | (23) | + | + | N/A | 100 | 12 | 9.30 | + | LN | N/A |
| | (24) | - | - | N/A | N/A | N/A | N/A | N/A | N/A | Died in anesthesia |

A.    4 weeks
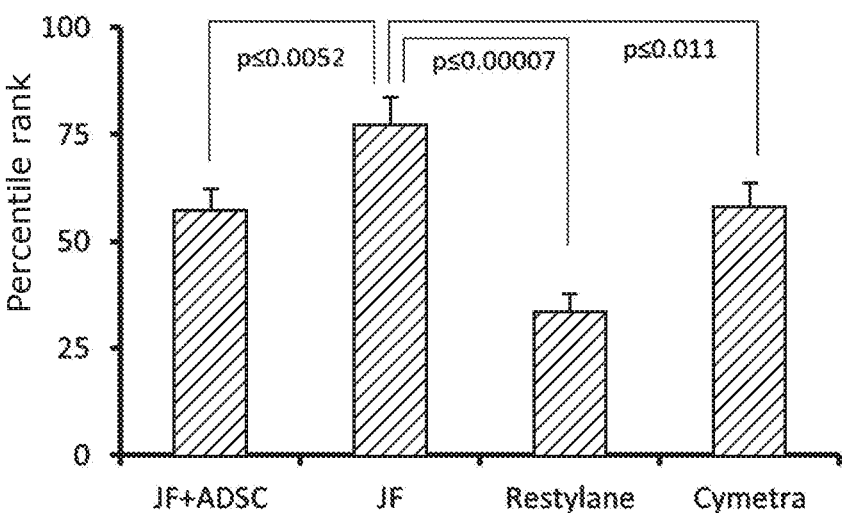
B.    12 weeks
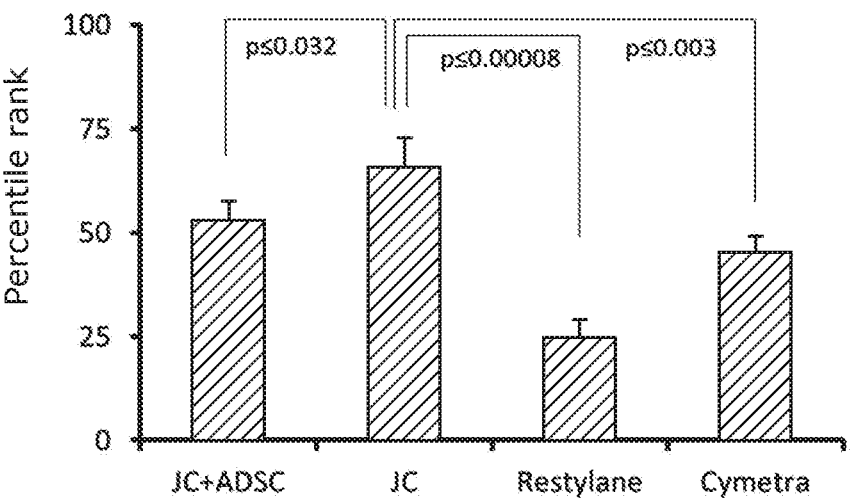
Figure 5

JELLYFISH COLLAGEN USE

PRIORITY CLAIM

This application is a national phase application under 35 U.S.C. § 371 of International Application No. PCT/GB2021/051491, filed Jun. 15, 2021, which claims the benefit of Great Britain Patent Application No. 2010544.1, filed Jul. 9, 2020, and U.S. Provisional Patent Application No. 63/039,716, filed Jun. 16, 2020, the entirety of each of which are incorporated herein by reference.

FIELD OF THE INVENTION

The present invention relates to jellyfish collagen for use in the treatment of vocal fold paralysis.

BACKGROUND OF THE INVENTION

The vocal folds (VFs) are instrumental for voice communication and glottal competence and unilateral true VF paralysis (UVFP) disrupts these functions. UVFP is reportedly three times more prevalent than bilateral vocal fold paralysis. UVFP has a multifactorial etiology with approximately 80% of cases either idiopathic, secondary to heart and lung disease or non-thyroid malignancy. Thyroidectomy is a major risk factor for UVFP accounting for the remaining ~20% of cases (Spataro et al, 2014. *Otolaryngol. Head Neck Surg.,* 151:286-293). Indeed, thyroidectomy has almost doubled over in the years from 2005 to 2020 due to increased incidence and early diagnosis of thyroid disease and over 10,000 patients each year in the US require treatment for UVFP. Because the recurrent laryngeal nerve (RLN) runs in intimate association with the thyroid gland, accidental injury or sectioning can occur during thyroidectomy.

Injection medialisation laryngoplasty (IL) is a first line treatment for UVFP and is aimed at restoring glottic closure and phonation. Typically, a volume-augmenting material is injected into the thyroarytenoid space, lateral to the paralyzed VF for the purpose of bringing it near to the contralateral VF. This process is referred to as medialisation. Medialisation results are temporary and vary according to the materials used and type of immune responses. The procedure has a history of more than 100 years and was pioneered in 1911 by Bruening, using paraffin. Because synkinetic RLN reinnervation may occur within 6 to 8 months after VFP, IL was initially performed as a temporary measure. More recent outcome data suggest that when compared to IL, reinnervation may not warrant the extra challenges associated with microneural surgery (Siu et al, 2016. *Laryngoscope,* 126:1616-1624).

Over the years, the field of biomaterials has gradually shifted towards compounds that are relatively easy to inject with smaller bore needles and under local anaesthesia, are well tolerated, do not migrate, and require fewer visits to the doctor's office (Eppley and Dadvand, 2006. *Plast. Reconstr. Surg.,* 118:98e-106e). Furthermore, many variations of the Bruening protocol and a large array of biomaterials have been described (Li et al, 2016. *Biomaterials,* 108:91-110; Mallur and Rosen, 2010. *Clin. Exp. Otorhinolaryngol.,* 3:177-182). Each biomaterial aims to achieve an optimal balance between ease and convenience of injection, duration of laryngeal closure and degree of restored phonation. In some cases, it may be desirable that an injectable is quickly resorbed when reinnervation is likely whereas in others, a longer lasting material may be preferable. Three compounds widely used in IL are calcium hydroxyl-apatite and its carboxymethyl cellulose carrier, cross-linked hyaluronic acid (e.g. Restylane® brand) and human cadaveric micronised acellular dermis (MACD) (e.g. Cymetra® brand). In addition to Cymetra® and Restylane® a variety of materials have been introduced on to the market that attempt to strike a balance between restoring glottal competence and phonation. For example, bovine gelatin (Gelfoam®), carboxymethylcellulose (Radiesse®), bovine collagen (Zyplast® and Zyderm®), calcium-hydroxylapatite, fat, and fascia. Restylane® and Cymetra® are the most commonly used IL products but they are relatively short lived, requiring multiple visits to the laryngologist office. Furthermore, Cymetra® is prepared from human cadaver skin meaning it is prone to batch-to-batch variability issues while bovine materials pose the risk of prion contamination. Other materials such as silk (Gulka et al, 2019. *Laryngoscope,* 129:1856-1862) and tissue-mimetic nano-fibrillar hybrids (Latifi et al, 2018. *Sci Rep.,* 8:1047) have also been considered for use in IL.

As mentioned above, glottal closure benefits for currently used IL biomaterials are typically short lasting requiring multiple visits to the clinic while the quality of phonation also varies. As such, there is a need for IL products that can be administered safely and with consistent results in the doctor's office, have long-term glottal closure benefits (thereby decreasing the need for repeated medical visits), and restore proper phonation. Accordingly, a biomaterial which would be suitable for use in the treatment of vocal fold paralysis by IL, without displaying the disadvantages discussed above, would be particularly advantageous.

SUMMARY OF THE INVENTION

The present invention relates to jellyfish collagen for use in the treatment of vocal fold paralysis. As will be evident from the data presented below, the inventors have surprisingly found that compositions comprising jellyfish collagen are useful in the treatment of vocal fold paralysis by IL as an alternative to currently used biomaterials (e.g. cross-linked hyaluronic acid and human cadaveric micronised acellular dermis), whilst demonstrating superior results in terms of vocal fold medialisation, as well as other superior qualities, including: minimal material migration in vivo, increased glottal benefit with minimal tissue pathology, low immunogenicity, tissue regeneration benefits (e.g. vascularisation), and a lower risk of virus transfer and/or disease/prion transmission. This is an entirely unexpected finding given the different physicochemical properties of jellyfish collagen compared to the prevailing biomaterials used in the treatment of vocal fold paralysis by IL.

Accordingly, a first aspect of the invention relates to a composition for use in the treatment of vocal fold paralysis, wherein the composition comprises jellyfish collagen.

A second aspect of the invention relates to a method of treating vocal fold paralysis, wherein the method comprises administering a composition comprising jellyfish collagen to a subject in need thereof.

A third aspect of the invention relates to the use of jellyfish collagen for the manufacture of a medicament for the treatment of vocal fold paralysis.

DESCRIPTION OF THE FIGURES

Embodiments of the present invention will now be described, by way of example only, with reference to the accompanying figures, in which:

FIG. 1 shows a table summarising the rabbit study and the principal findings. The "General Key" for the table is as follows: +=high confidence; +/-=medium confidence; -=low confidence; ADSC=adipose mesenchymal stem cells; IL=injection medialisation laryngoplasty; VFP=vocal fold paralysis. The "Histology Key" for the table is as follows: A=adipocytes infiltration; HN=histiocytic nodule (granuloma); LN=lymphocytic nodule; MA=muscle atrophy; MD/F=myocyte death/fibroplasia.

FIG. 5 shows percentile rank analysis of ellipsoid volumes at (A) 4-weeks after IL, and (B) 12-weeks after IL. Ellipsoid volumes were ordered from high to low and ranked on a 100 to 1 scale. Rank data was extracted for each group and statistical significance was determined using Kruskal-Wallis H-test (p<0.001). Individual groups differences were compared using the Mann-Whitney U test.

DETAILED DESCRIPTION OF THE INVENTION

Figure 2:
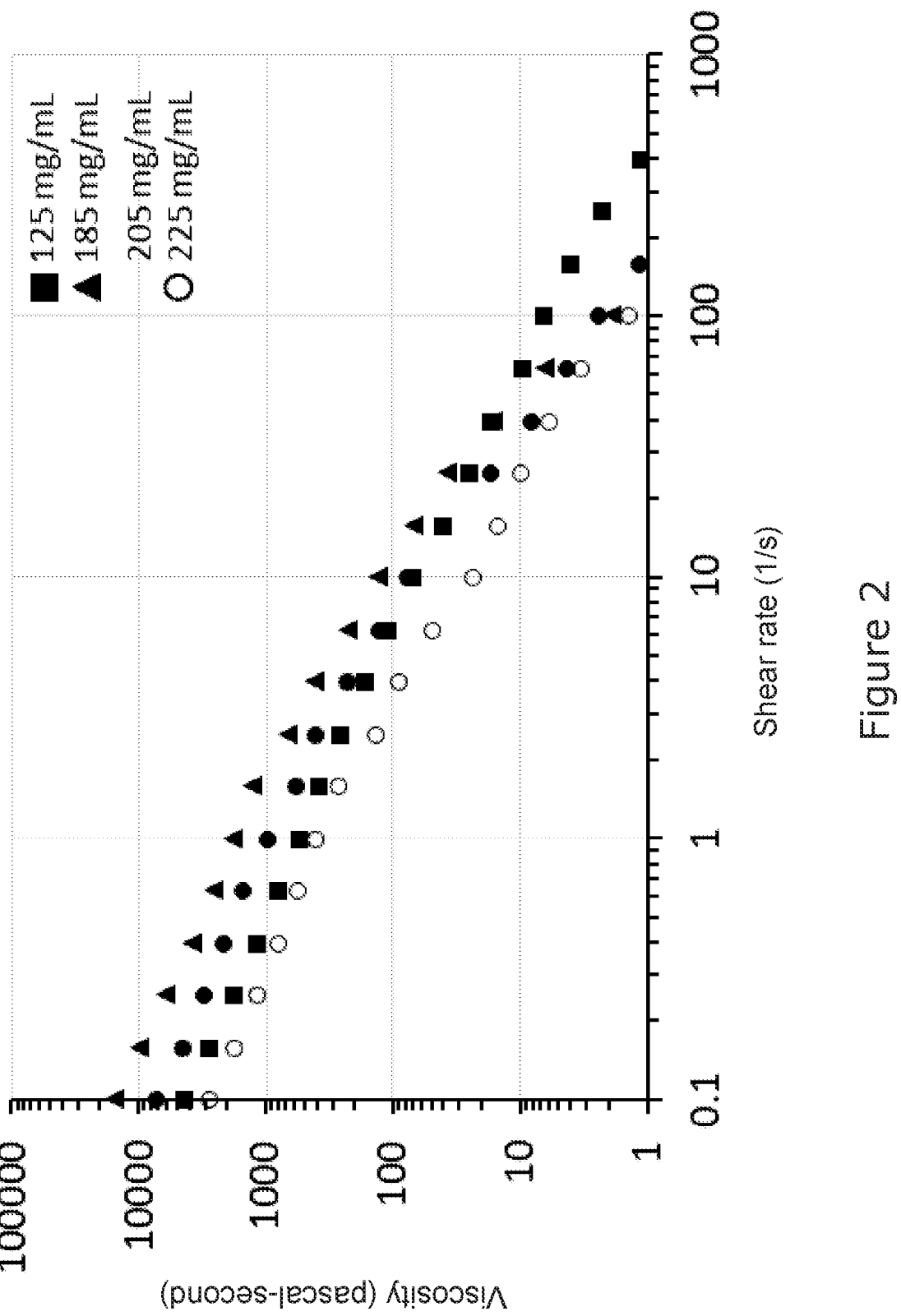
FIG. 2 shows rheological features of injected materials. (A). Rheological features of MX-JC solutions showing non-Newtonian, liquid thinning behavior. (B). Comparison of rheological features for Cymetra® (275 mg/mL), MX-JC (225 mg/mL), and Restylane® (20 mg/ml).
Figure 2:
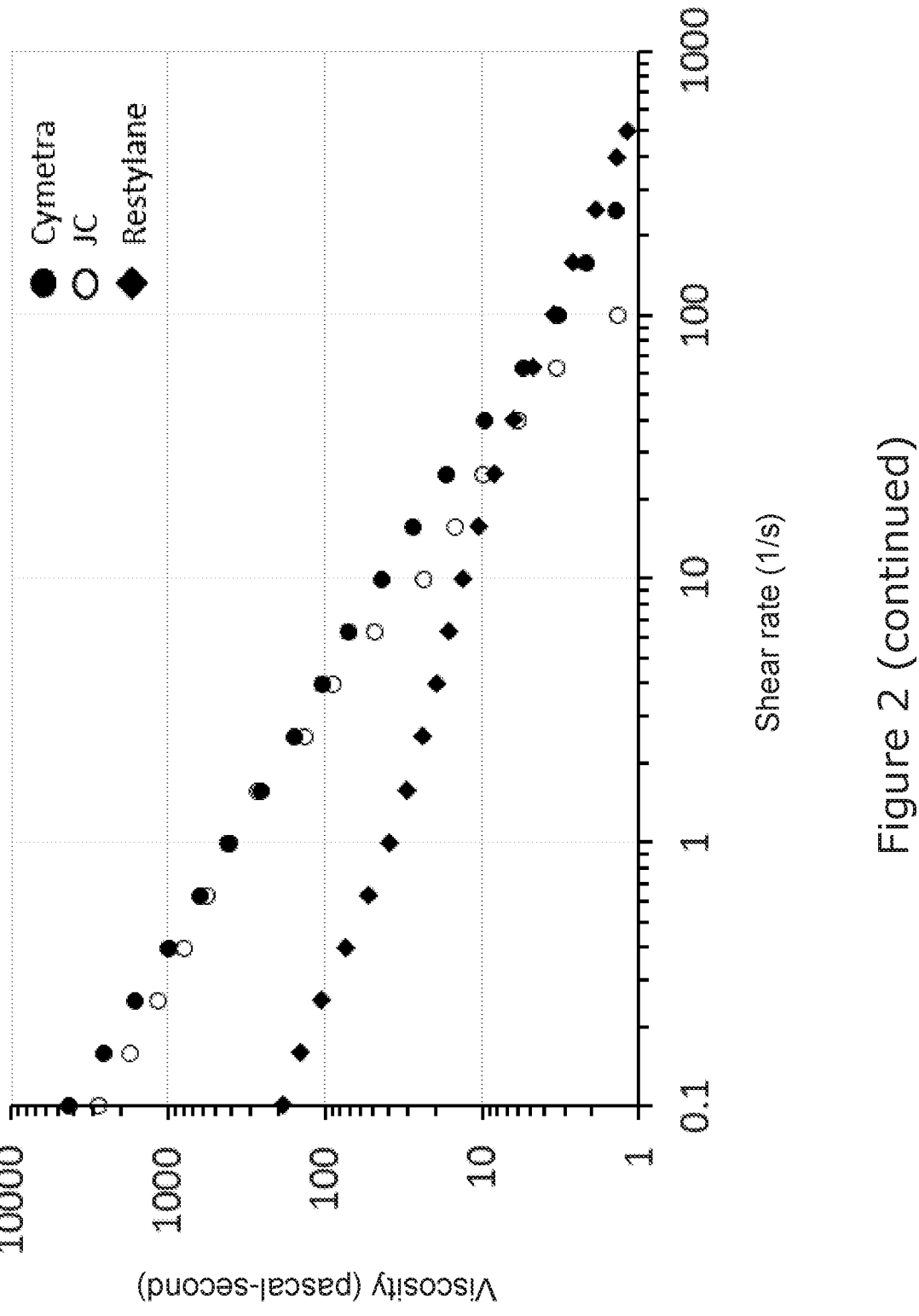

In the following detailed description, numerous specific details are set forth in order to provide a thorough understanding of the present invention. It will be understood by those of ordinary skill in the art that embodiments of the present invention may be practiced without these specific details while still remaining within the scope of the claims.

In a first aspect, the present invention provides a composition for use in the treatment of vocal fold paralysis, wherein the composition comprises jellyfish collagen.

In a second aspect, the present invention provides a method of treating vocal fold paralysis, wherein the method comprises administering a composition comprising jellyfish collagen to a subject in need thereof.

In a third aspect, the present invention provides for the use of jellyfish collagen for the manufacture of a medicament for the treatment of vocal fold paralysis.

In some embodiments, the vocal fold paralysis is unilateral true vocal fold paralysis (UVFP) or bilateral vocal fold paralysis (BVFP). In a preferred embodiment, the vocal fold paralysis is unilateral true vocal fold paralysis (UVFP).

By "vocal fold paralysis" we include the meaning of an injury to one or both recurrent laryngeal nerves (RLNs) leading to disruption of nerve impulses to the laryngeal muscles. Paralysis of one RLN is referred to as unilateral true vocal fold paralysis (UVFP) and paralysis of both RLNs is referred to as bilateral vocal fold paralysis (BVFP).

Potential causes of vocal cord paralysis include, but are not limited to, general trauma to head and neck area, nerve damage during surgery, congenital conditions, infectious causes (e.g. viral or bacterial infection), endocrinologic diseases (e.g. thyroid disease), systemic neurologic diseases, and certain cancers.

In some embodiments, wherein the treatment of vocal fold paralysis is by injection medialisation laryngoplasty (IL).

By "injection medialisation laryngoplasty (IL)" we include the meaning of injection of a filler material into the thyroarytenoid space at a position lateral to the paralysed vocal fold for the purpose of bringing it near to the contralateral vocal fold. Such procedures aim to improve phonation and glottal closure in patients.

In some embodiments, the jellyfish collagen is in its atelo form. By "atelo form" we include the meaning of a low-immunogenic derivative of collagen obtained by removal of N- and C-terminal telopeptide components, which are known to induce antigenicity in humans. Telopeptides are generally removed by treatment of collagen with type I pepsin.

In some embodiments, the jellyfish collagen is in its telo form. By "telo form" we include the meaning of a collagen extracted in acid conditions producing a soluble collagen that includes telopeptides.

In some embodiments, the jellyfish collagen is thiolated. The term 'thiolated' is intended to refer to a jellyfish collagen which has been reacted with a thiol, resulting in the introduction of a —SH group, or 'thiol' group.

In some embodiments, the jellyfish collagen is methacrylated. By "methacrylated" we include the meaning of a collagen in which methacrylate groups have been added to produce collagen methacrylamide In preferred embodiments, the jellyfish collagen is cross-linked. In the context of the present invention, the term 'cross-linked' refers to the linkage of two independent collagen molecules via a covalent bond.

It is envisaged that any cross-linking agent known to cross-link under the conditions within which collagen fibrils are formed would be a suitable cross-linking agent for use in the invention. For example, the jellyfish collagen of the invention may be crosslinked using a cross-linking agent such as EDC, Genipin, 1,4-BDDGE, Polyethylene glycol (PEG), or mucochloric acid. Preferably, the cross-linking agent is EDC. The EDC may be at a concentration of 0.01% to 5%, 0.05% to 5%, 0.1% to 5%, 0.2% to 5%, 0.3% to 5%, 0.4% to 5%, 0.5% to 5%, 0.6% to 5%, 0.7% to 5%, 0.8% to 5%, 0.9% to 5%, 1% to 5%, 1.5% to 5%, 2% to 5%, 3% to 5%, 3.5% to 5%, 4% to 5%, or 4.5% to 5%. Preferably, the concentration of EDC is 0.5% to 1%.

The source of the jellyfish collagen may be from the sub-phylum Scyphozoa. In some embodiments, the source of the jellyfish collagen may be selected from the group consisting of: the order Rhizostomeae, including, but not limited to, *Rhizostomas pulmo, Rhopilema esculentum, Rhopilema nomadica, Stomolophus meleagris, Cassiopea* sp. (upside-down jellyfish), including but not limited to *Cassiopea andromeda*, the order Semaeostomease, including *Aurelia* sp., and other species such as *Nemopilema nomurai, Rhopilema esculentum, Rhopilema nomadica, Stomolophus meleagris*, or any combination thereof. Preferably the source of the jellyfish collagen is *Rhizostomas pulmo*. Accordingly, the collagen may comprise at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, at least 99% *Rhizostomas pulmo* collagen.

The jellyfish may be formulated as a powder, such as a micronised powder, a hydrogel, a paste, a membrane, a scaffold, a solution, a sponge matrix, a nano-fibre electro-spun matrix, or in a lyophilised form. A 'hydrogel' is a network of polymer chains that are hydrophilic, resulting in a highly absorbent material. The term 'paste' is intended to refer to a semisolid preparation. In a preferred embodiment, the jellyfish collagen is in the form of a micronised powder.

In some embodiments, the jellyfish collagen has a particle size of 1 μm to 1000 μm, preferably a particle size of 100 μm to 500 μm, more preferably a particle size of 200 μm to 400 μm. The jellyfish collagen may have a particle size of 50 μm to 950 μm, 75 μm to 900 μm, 100 μm to 850 μm, 125 μm to 800 μm, 150 μm to 750 μm, 175 μm to 700 μm, 200 μm to 650 μm, 225 μm to 600 μm, 25 μm to 550 μm, 275 μm to 500 μm, 300 μm to 475 μm, 325 μm to 450 μm, 350 μm to 425 μm, 375 μm to 400 μm.

In some embodiments, the jellyfish is at a concentration of 1 to 500 mg/mL, preferably at a concentration of 50 to 400 mg/mL, more preferably at a concentration of 100 to 300 mg/mL, yet more preferably at a concentration of 200 to 300 mg/mL, most preferably at 200 mg/mL to 250 mg/mL. The jellyfish collagen may be at a concentration of 25 mg/mL to 475 mg/mL, 50 mg/mL to 450 mg/mL, 75 mg/mL to 425 mg/mL, 100 mg/mL to 400 mg/mL, 125 mg/mL to 375 mg/mL, 150 mg/mL to 350 mg/mL, 175 mg/mL to 325 mg/mL, 200 mg/mL to 300 mg/mL, 225 mg/mL to 275 mg/mL, or 200 mg/mL to 250 mg/mL.

The composition comprising jellyfish collagen according to the invention may, in some embodiments, further comprise adipose derived mesenchymal stem cells (ADSCs). Protocols for the preparation of ADSCs are well-known in the art and could be followed by the skilled person as a matter of routine. For example, a method of preparing ADSCs is described in Oldenburg et al, 2018. *Laryngoscope*, 128(1): 160-167.

The composition comprising jellyfish collagen according to the invention may further comprise a pharmaceutically acceptable excipient and/or carrier, and/or a pharmaceutically active ingredient. The excipients and carriers may enhance stability and/or improve the biopharmaceutical profile of the pharmaceutically active ingredient or the jellyfish collagen, which may or may not have an active substance conjugated. Examples of suitable pharmaceutically acceptable excipients and carriers may include sterile water, lidocaine, olive oil, ethyl oleate, glycols, monosaccharides such as fructose, glucose and galactose; non-reducing disaccharides such as sucrose, lactose and trehalose; non-reducing oligosaccharides such as raffinose and melezitose; non-reducing starch derived polysaccharide products such as maltodextrins, dextrans and cyclodextrins; and non-reducing alditols such as mannitol and xylitol. Further suitable excipients include cellulose preparations such as maize starch, wheat starch, rice starch, potato starch, gelatin, gum tragacanth, and/or polyvinylpyrrolidone. Mixtures of two or more of any of the above excipients or carriers (or any other suitable equivalent) are also envisaged. It is understood that any other substance with a similar effect would also be suitable.

There are multiple methods for 'isolating', or 'purifying', jellyfish collagen from the anatomical milieu. Many of these will be well known and routine to the skilled person. For example, collagen can be purified from jellyfish by acid extraction, whereby different anatomical parts of the jellyfish are bathed in an acidic solution. 'Bathing', or 'bathed', refers to the process of incubating the jellyfish in the acid solution for a sufficient amount of time in order to liberate the collagen molecule. An alternative method of collagen purification is enzyme extraction, whereby the jellyfish is incubated with at least one proteolytic enzyme for a sufficient amount of time and under conditions that favour the degradation of the anatomical milieu in order to liberate the collagen molecule. The exact temperature, pH and incubation time of the enzyme extraction method will vary depending on the proteolytic enzyme used. The most suitable conditions will be well known to the person skilled in the art. By way of non-limiting example, the enzyme pepsin can be incubated with jellyfish under acidic conditions in order to liberate the collagen molecule. It is envisaged that any enzyme can be used in the enzyme extraction method, and the above examples are intended to be in no way limiting.

The collagen can then be further isolated, or purified, from the undesired contaminants of the acid or enzyme extraction method by a number of different means. For example, insoluble contaminants can be removed by centrifugation. If a purer source of collagen is required, the isolated collagen can be subjected to gel filtration, or an alternative chromatographic method that would enable the purification of the collagen molecule for other soluble contaminants of the extraction process. The exact method of further purification is not particularly limiting. Any method well known and routinely used by a protein biochemist could be adapted for the purpose of obtaining purified, or isolated, jellyfish collagen. This step can also enable the transfer of the jellyfish collagen into the desired storage buffer in order to obtain the desired solution of purified jellyfish collagen. This can be achieved by first equilibrating the chromatographic apparatus with the desired storage buffer before purification. There exist many alternative, well known methods that could be used for this purpose. Preferably, the collagen used in the invention is from 70% to 99% pure, wherein pure refers to the % wt in a solution that is attributable to the collagen molecule. More preferably, the collagen solution is at least 95%, 96%, 97%, 98%, or 99% pure.

The present invention is now further described with reference to the below examples and studies.

EXAMPLES

Example 1: Study Design and Animals

Materials and Methods

Following approval of the protocol by the Institutional Animal Care and Use Committee (IACUC A4201) a total of 24, three-week-old female New Zealand White rabbits (average weight at arrival 3.12±0.18 kg) were divided into four groups of N=6 each based on power calculations (1-β=80%, p<0.05) using previous findings (Oldenburg et al, 2018. *Laryngoscope,* 128(1): 160-167).

The four test groups were:

Group 1: Rabbits receiving micronised cross-linked jellyfish collagen (MX-JC) and adipose derived mesenchymal stem cells (ADSCs).

Group 2: Rabbits receiving MX-JC.

Group 3: Rabbits receiving cross-linked hyaluronic acid (X-HA)(Restylane®).

Group 4: Rabbits receiving micronised acellular dermis (MACD)(Cymetra®).

The protocol is described in detail elsewhere (Oldenburg et al, 2018. *Laryngoscope,* 128(1): 160-167; Oldenburg et al, 2017. *Laryngoscope,* 127(5): E166-E169). Briefly, rabbits were acclimatised for 2 weeks before surgery for RLN sectioning and fat collection that was conducted sequentially. Anaesthesia was induced with intramuscular ketamine 42 mg/kg, xylazine 6 mg/kg, and acepromazine 1.2 mg/kg, and maintained with 1-2% isoflurane. Buprenorphine 0.18 mg/kg and carprofen 1.5 mg/kg were used to control post-operative pain. The left RLN was located by blunt dissection along the inferior thyroid artery and a 1-cm section was removed. A piece of fat approximately 1.5 cm in diameter was collected from the cricotracheal area and placed in sterile saline solution. Only fat from Group 1 was further processed for ADSC expansion and injection. Two weeks later animals were re-anaesthetised for IL, the larynx was exposed, and image guided endoscopy was used to visualise needle location and injection delivery. IL was performed with 23-gauge needles, aiming to deliver the material lateral to the vocal process of the arytenoid cartilage. For each animal, 100 µL were injected using a 1-mL syringe. MX-JC (225 mg/mL) was reconstituted from dry powder with pH-buffered saline at the time of injection and warmed up to 37° C. to facilitate mixing. For Group 1, reconstituted MX-JC was mixed with 1×10⁶ ADSCs and 5 ng/mL of TGF-β2 prior to injection and delivered into the same animal from which it was harvested. Cymetra® (275 mg/mL) and Restylane® (20 mg/mL) were injected according to the manufacturers' specifications. Contemporaneous notes and video recording were performed for both surgery and IL to immortalise details, such as extent of RLN paralysis, location of the needle, net volume of material injected, and complications arising during surgery or post-op recovery. Animals were weighed at arrival, after surgery and once a week thereafter to monitor overall health.

Preparation of ADSCs was performed as previously described (Oldenburg et al, 2018. *Laryngoscope,* 128(1): 160-167). Briefly, adipose tissue was minced with scalpels and digested with 3-5 mL of 0.15% collagenase type 1 solution (C0130-1G; Sigma, St. Louis, MO) in Advanced MEM media (A-MEM, Life Sciences) containing 10% fetal bovine serum (FBS), 1% GlutaMAX, and 1 mg/mL penicillin/streptomycin solution. Cells were separated from the fat layer by 1.5 hours incubation with occasional shaking at 37° C. followed by centrifugation at 500 g for 5 minutes. The pellet was washed with phosphate-buffered saline, strained through a 70 µm sieve to remove large particulate matter, reconstituted by centrifugation for 5 minutes at 500 g, and finally resuspended in 5-10 mL of A-MEM media for overnight incubation at 37° C., in 5% CO2, and 95% humidity atmosphere. The following day, nonadherent material was removed, and fresh media added. Media changes were every 2 to 3 days. Cells were passaged 1:2 at 60-80% confluence. Passage 3 cells were cryopreserved and freshly expanded for 24-48 hours before IL. A total of 1×10⁶ ADSCs were co-injected with MX-JC in Group 1 rabbits only.

Results

Animal data are summarised in the table in FIG. 1. One animal in Group 4 died from anaesthesia and was not replaced. No other animals were lost due to surgical procedures, post-operatory care, or complications from the protocol. Experimental success rates were determined by analysis of videos and contemporaneous notes. For RLN surgery 21/23 animals (~91%) displayed paralysis of the left VF. One animal had partial VFP and one had no VFP (Group 3). Injections that delivered 100 µL into the left thyroarytenoid space were scored as "high confidence", all others as "medium-low confidence". Approximately 70% of all injections were "high confidence". Volumes exceeding 100 µL and material extrusion and/or deviation from the delivery site accounted for, respectively, 22% and 8% of "medium-low confidence" injections. Because of the difficulty of co-injecting ADSCs with MX-JC, five animals in Group 1 (83%) received the IL injection with "medium-low confidence". Regardless of treatments rabbits fed normally throughout the experiment and gained weight as expected (data not shown).

Example 2: Viscosity and Rheology Testing

Materials and Methods

To help understand the materials' behavior during injection, rheological properties of the three compounds were evaluated using a DHR-1 Discovery Hybrid Rheometer (TA Instruments, New Castle, DE, USA) equipped with a 40 mm parallel Peltier plate geometry. Dynamic viscoelasticity was measured as a function of frequency in the linear viscoelastic region using 1.0 mL of sample. Test temperature=39° C.; soak time=0 seconds; shear rate=0.1 to 500 s⁻¹; max equilibration time=60 seconds; and, sampling period=30 seconds.

Results

MX-JC of average particle size 300 µm was homogenised in phosphate-buffered saline using an interconnected two syringe assembly. To generate an injectable of desirable viscosity, concentrations ranging from 60-300 mg/ml were tested for tactile consistency and rheological characteristics. Overall, there was a trend towards an asymptotic decrease in viscosity at higher shear rates as the concentration increased (FIG. 2A). MX-JC, Restylane®, and Cymetra® displayed non-Newtonian, liquid thinning behavior. Deformation curves for Cymetra® (275 mg/ml) and MX-JC (225 mg/mL) ran almost parallel, while the Restylane® (20 mg/mL) curve showed the highest resistance to thinning (FIG. 2B). This rheology analysis confirmed that MX-JC and Cymetra® had similar liquid-thinning properties.

Example 3: MRI Analysis

Materials and Methods

MRI analysis was carried out on material obtained from the animals described in Example 1. NMR experiments were performed using an Avance III 300 MHz (7 T) wide bore NMR spectrometer equipped with micro-imaging accessories (Bruker, BioSpin, Billerica, MA) and a 20 mm diameter volume coil. Specimens taken out of fixative were gently dried with tissue paper, transferred into 20 mm tubes, and tightly secured in the middle of the tube with a custom-made Teflon holder. Tubes were filled with Fluorinert FC-770

(3M, St. Paul, MN), a perfluorinated, proton-free solvent that helps improve the field homogeneity around the specimen but does not contribute to the background signal. Images were acquired with the core temperature of the gradient coil at 21° C.-25° C. To visualise the specimens, a Rapid Acquisition with Refocused Echoes (RARE) sequence was used, with the following parameters:

a) Repetition time: 4000 ms;
b) Echo time: 10.37 ms;
c) RARE factors: 12;
d) FOV: 16 cm×16 cm;
e) Matrix: 160×160;
f) Slice Thickness: 0.5 mm;
g) In Plane Resolution: 100 um/pxl;
h) Slice Thickness: 0.5 mm; and,
i) Acquisition time: 10 m 24 s.

Figure 3:
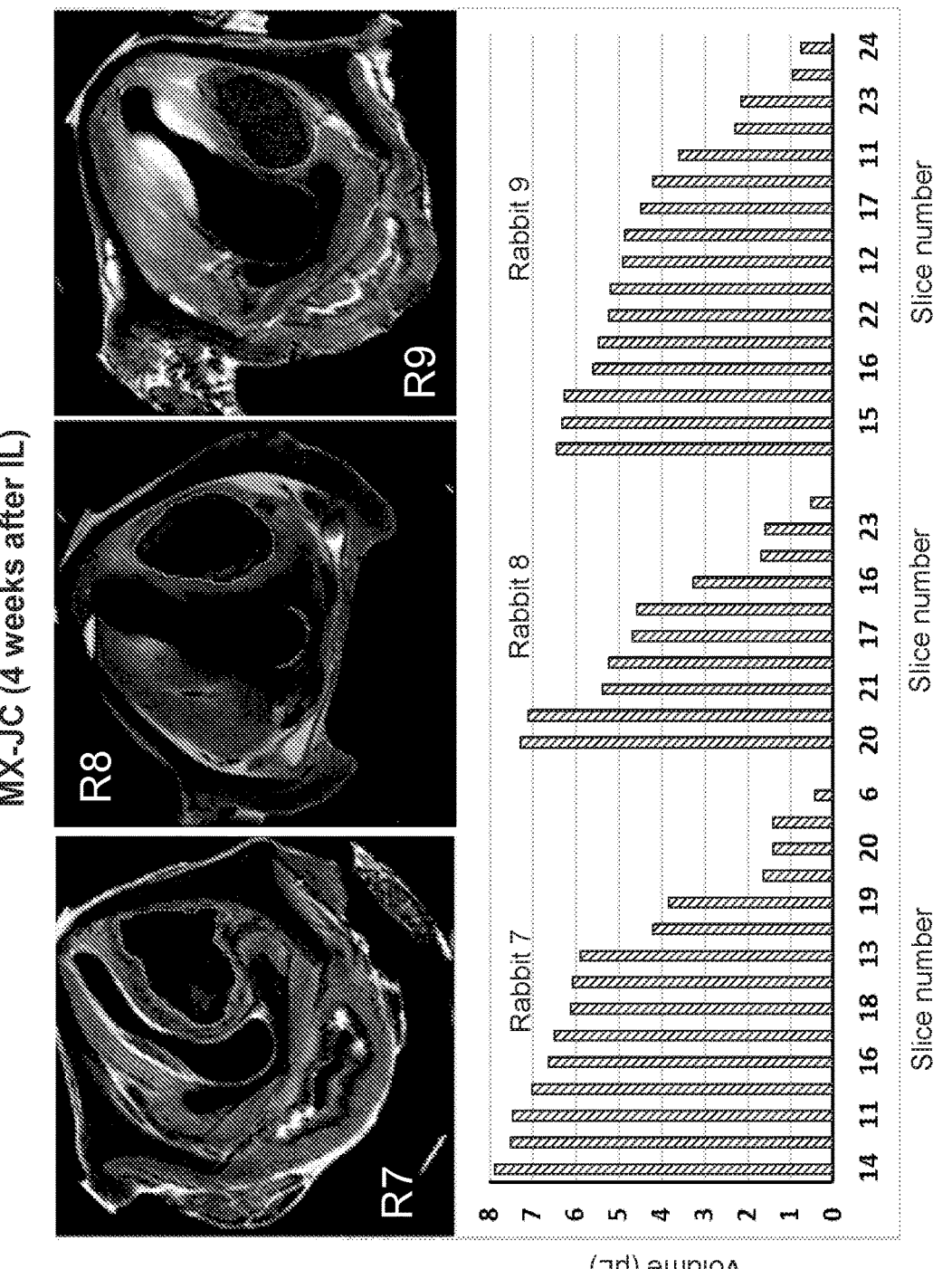
FIG. 3 shows MRI images and volume calculations at 4 weeks after injection medialisation laryngoplasty (IL). Upper panels: MRI images corresponding to the largest medialisation ellipsoids for all 11 animals tested. The rabbit number as listed in the table in FIG. 1 is indicated on each panel. Lower panels: Digital "slice" volumes for all animals, ordered from high to low. The X-axis corresponds to "slice number" and the y-axis represents the volume in microliters (μL). (A). Micronised cross-linked jellyfish collagen (MX-JC)+adipose derived mesenchymal stem cells (ADSCs). (B). MX-JC only. (C). Cross-linked hyaluronic acid (X-HA) (Restylane® brand). (D). Micronised acellular dermis (MACD) (Cymetra® brand).
Figure 3:
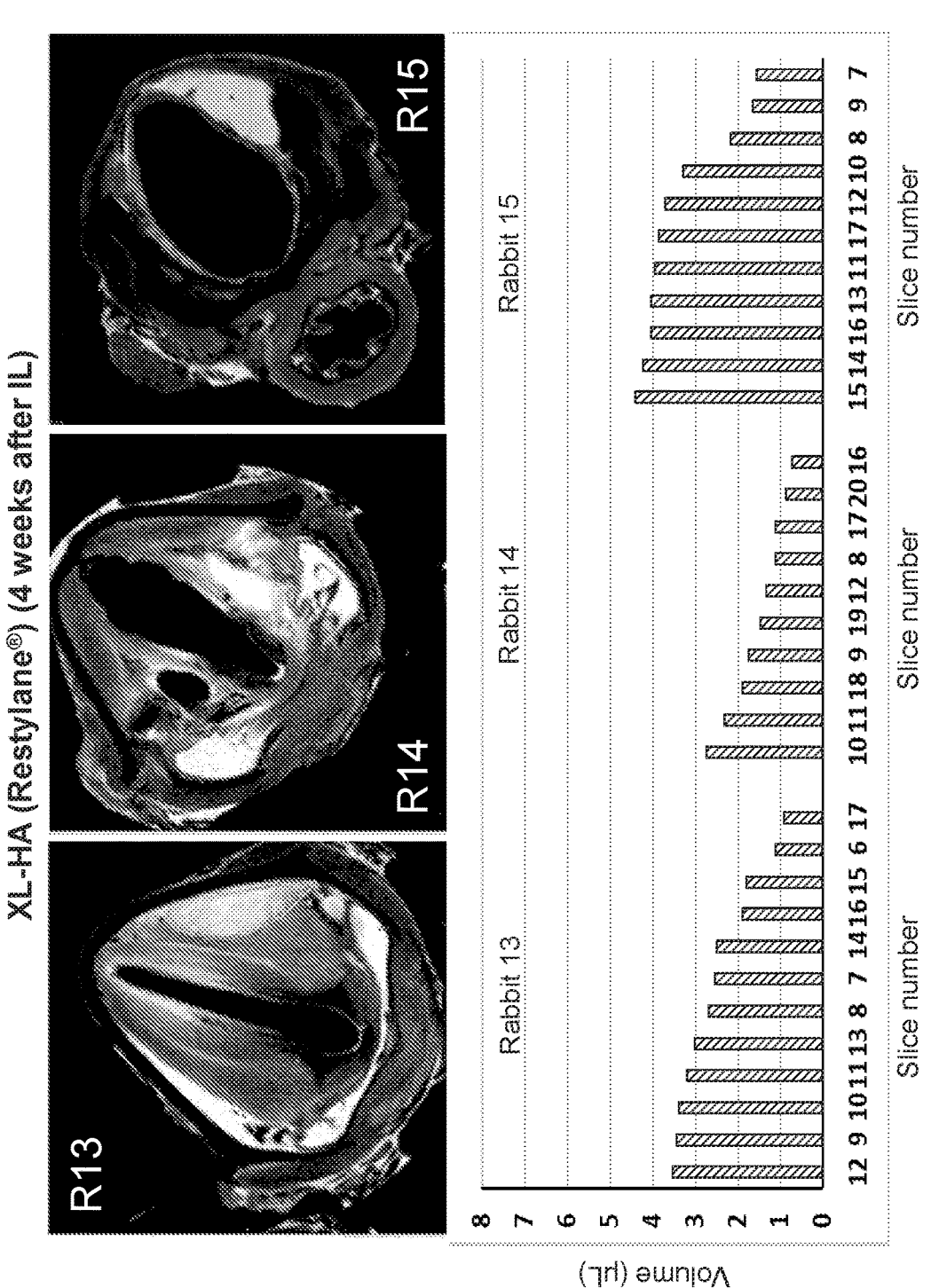
Figure 3:
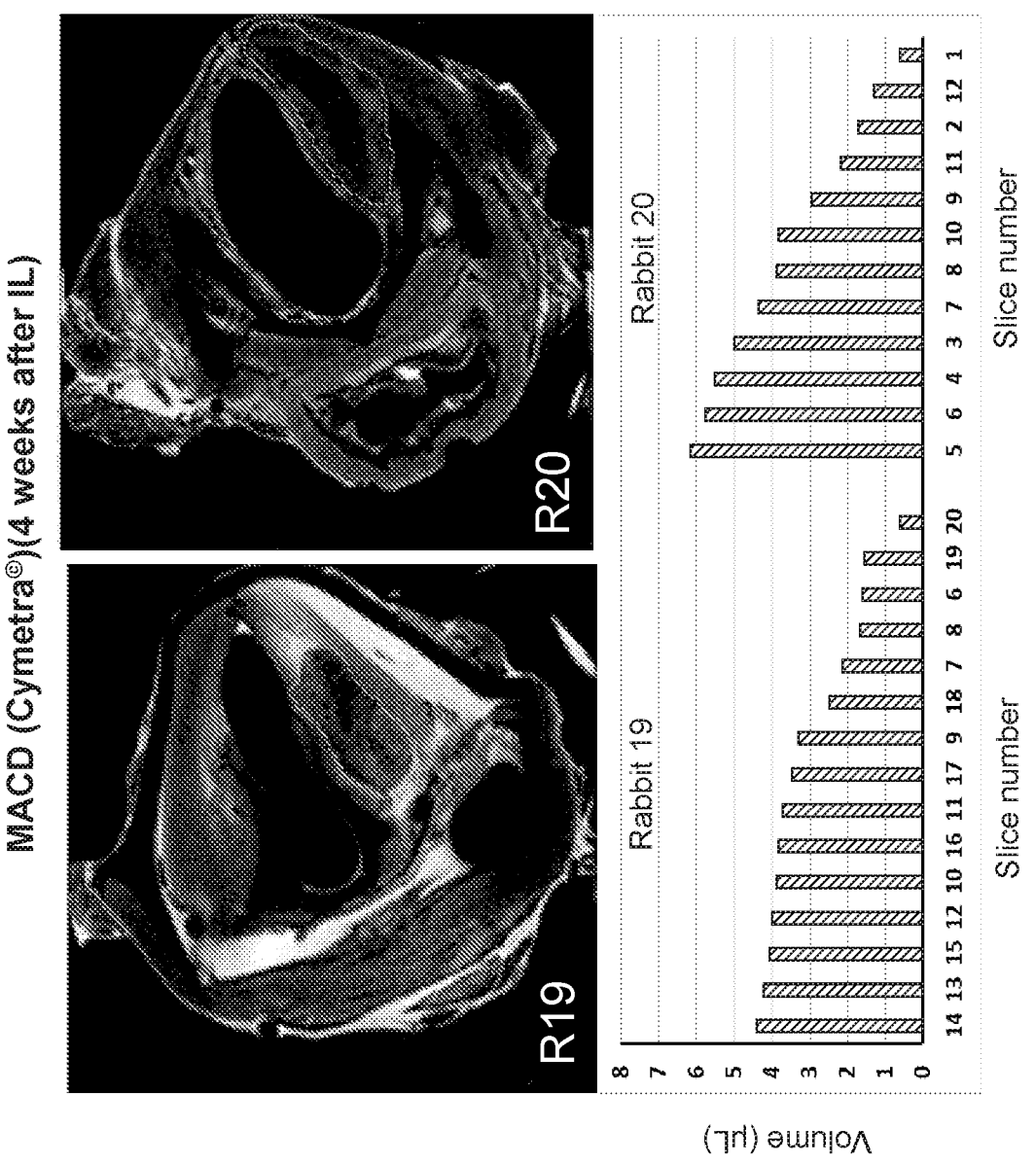
Figure 4:
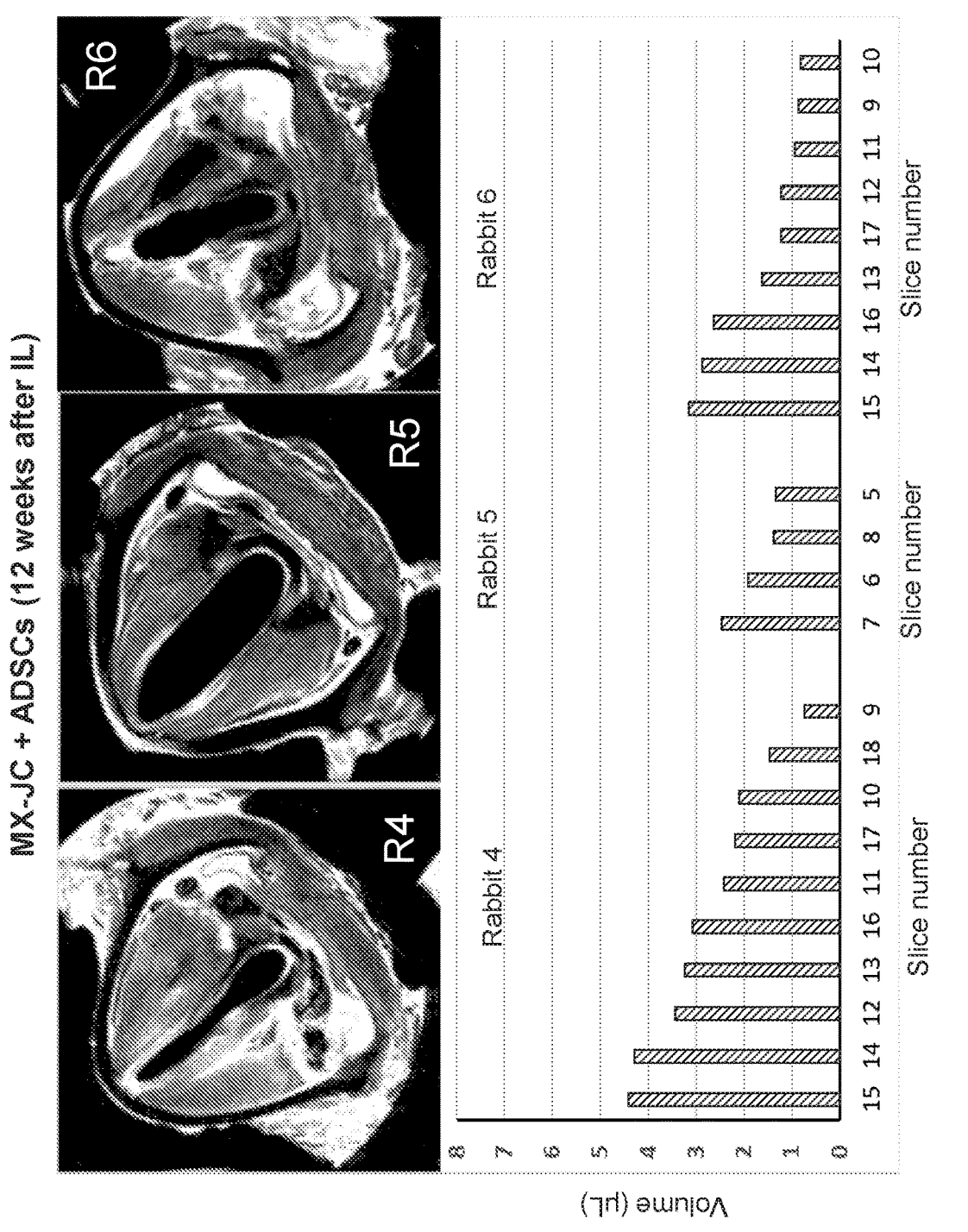
FIG. 4 shows MRI images and volume calculations at 12 weeks after injection medialisation laryngoplasty (IL). Upper panels: MRI images corresponding to the largest medialisation ellipsoids for all 11 animals tested. The rabbit number as listed in the table in FIG. 1 is indicated on each panel. Lower panels: Digital "slice" volumes for all animals, ordered from high to low. The X-axis corresponds to "slice number" and the y-axis represents the volume in microliters (μL). (A). Micronised cross-linked jellyfish collagen (MX-JC)+adipose derived mesenchymal stem cells (ADSCs). (B). MX-JC only. (C). Cross-linked hyaluronic acid (X-HA) (Restylane® brand). (D). Micronised acellular dermis (MACD) (Cymetra® brand).
Figure 4:
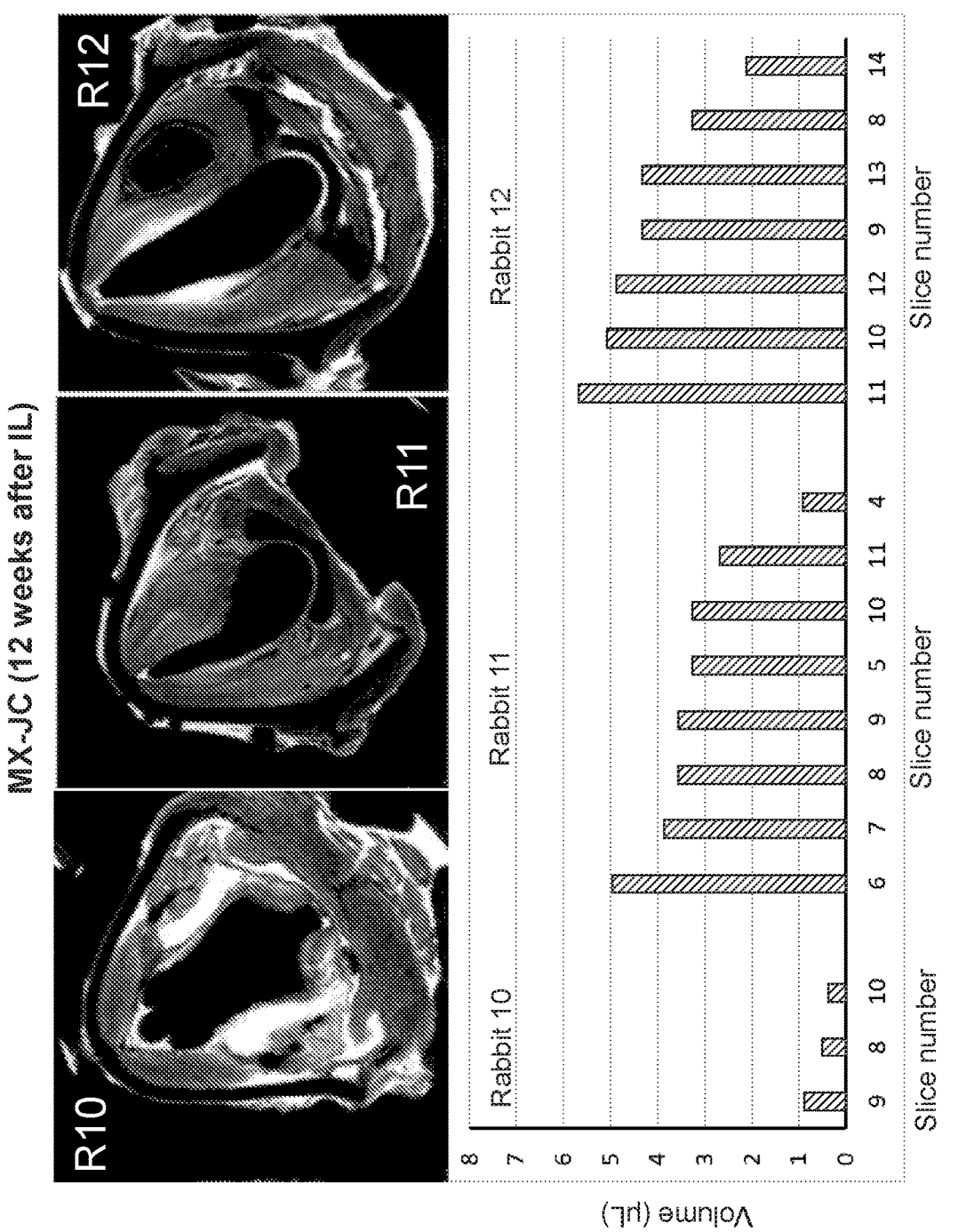
Figure 4:
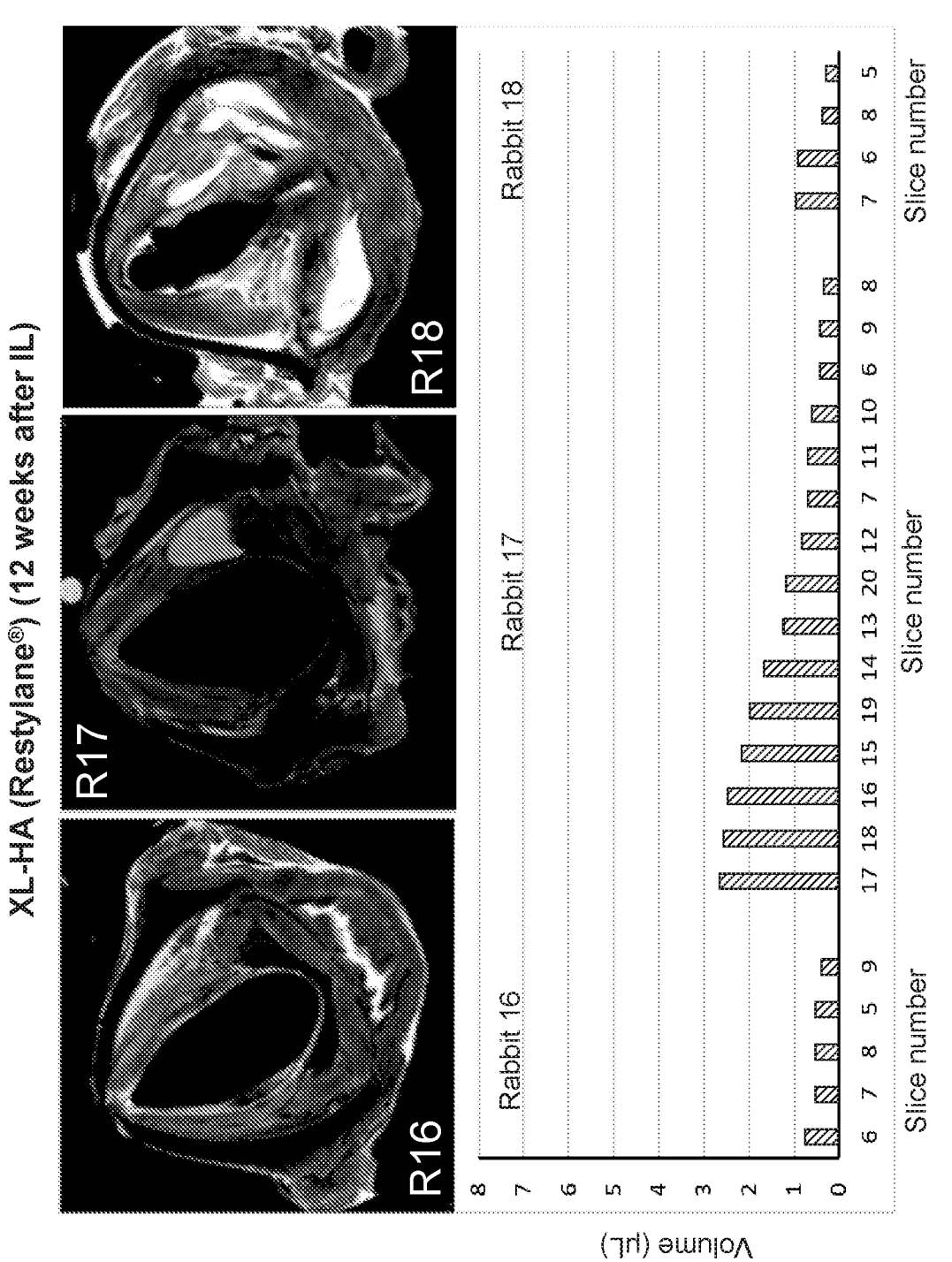
Figure 4:
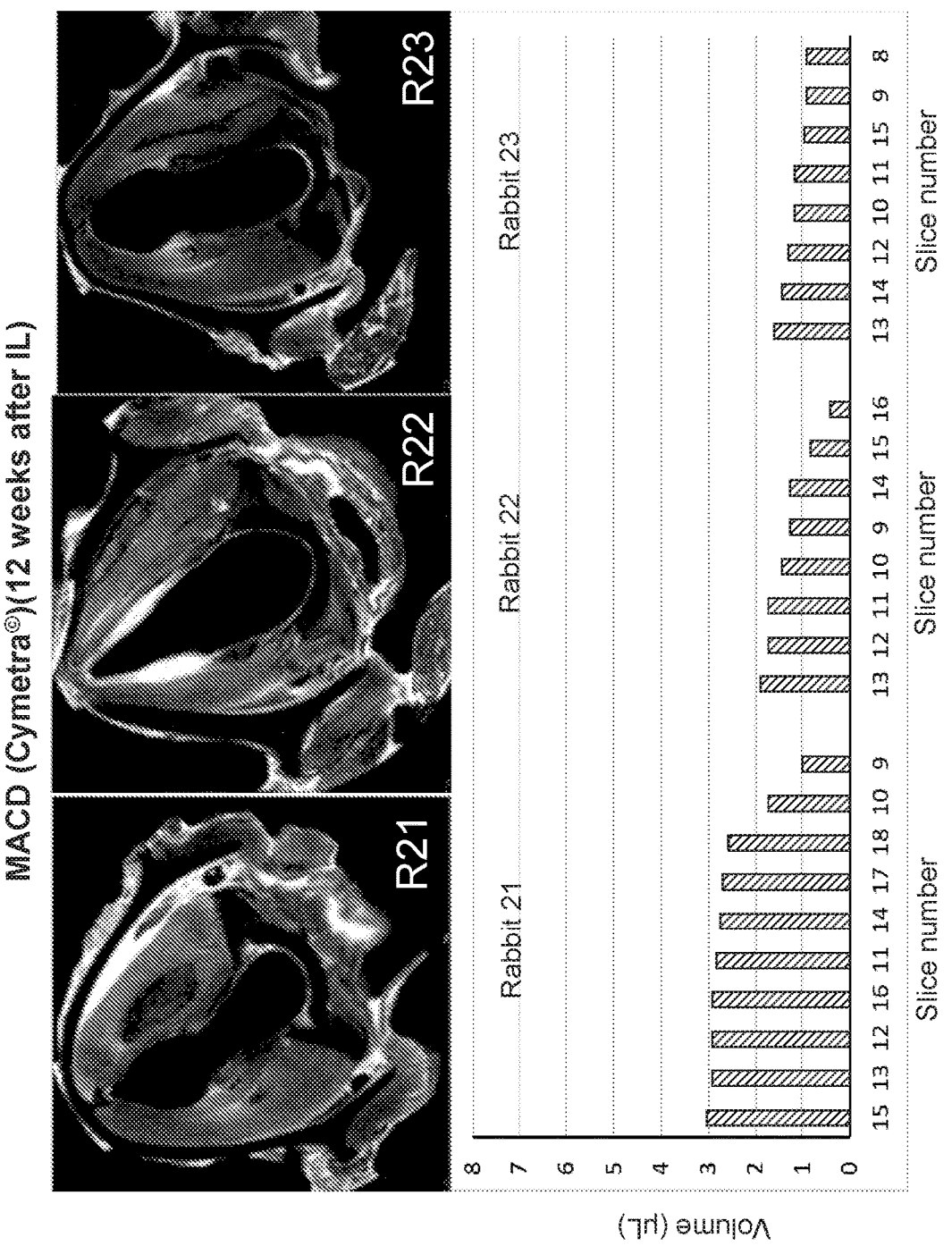

A slice and 3D protocol were compared for maximum feature resolution. The slice protocol consisted of 26, 0.5 mm digital "sections" of the larynx starting from the cricothyroid cartilage and moving in a superior direction. To identify start and end location of the medialisation material an initial short scan (3-5 slices) was performed after which a "digital box" containing the bulking material was constructed and sliced as above. With the 3D protocol 400 images spaced 0.005 mm apart were acquired overnight.
Statistical Analysis Group size for 80% statistical power and 0.05 was determined according to:

$$N = 16\frac{s^2}{d^2}$$

Where "s" is the standard deviation and "d" the difference between population means (Lehr, 1992. *Stat. Med.*, 11(8): 1099-1102). For volumetric analysis, each of the 26 MRI digital "slices" from all 23 animals was separately scored by three independent observers to help limit observational bias. MRI images were converted to DICOM format and volume analysis was performed using Analyze software (Mayo Clinic) or ImageJ. When needed, ellipsoids were confirmed by histology. To determine statistical differences between the groups, ellipsoids were ordered according to size and ranked. Kruskal-Wallis ANOVA of group ranks was performed with 0.05 threshold for statistical significance. Individual group differences were compared with Mann-Whitney U test and statistical significance was assigned at 0.05.
Results Twenty-six MRI images of the larynx spaced 0.5 mm apart were recorded for each animal, starting at the cricoid landmark and moving in a superior direction. Images depict medialisation ellipsoids caused by the injected materials as well as non-injected tissue situated above and below the injection sites. Overall, 46% of all MRI images at 4 weeks and 29% at 12 weeks reveal injected material, a ~37% decrease (p=0.002) that is likely due to resorption over time. Resorption rates were different for each material (see in the table in FIG. 1 and volume data calculation below). Highest resorption rate was in Group 3 (58%), followed by Group 4 (47%), Group 1 (31%), and lastly Group 2 (29%). Ellipsoid areas calculated using Analyze or ImageJ were multiplied by the digital "slice" thickness (0.5 mm) to yield volumes in μL (FIGS. 3 and 4). MRI images depict size and position of the largest ellipsoid for each animal sacrificed at 4 weeks (FIGS. 3A, 3B, 3C, and 3D, top panels) and 12 weeks (FIGS. 4A, 4B, 4C, and 4D, top panels). Volume data are shown for each animal ordered from highest to lowest. X-axes depict image numbers and y-axes volumes in μL (FIGS. 3 and 4, bottom panels).

Group 1 data consisted of 31 ellipsoids at 4 weeks and 23 at 12 weeks (N=54); Group 2, 41 and 18 (N=59); Group 3, 33 and 24 (N=57); and Group 4, 27 and 26 (N=52). When 4-weeks and 12-weeks data are collapsed the volume of material (mean±SD) remaining after IL was: Group 1, 2.72±1.34 μL, Group 2, 4.06±2.13 μL, Group 3, 1.88±1.25 μL, and Group 4, 2.49±1.44 μL. The Group 2 mean volume was statistically significantly higher than Groups 1,3 and 4 (p<0.0009). In order to further compare differences in ellipsoid sizes across all groups, as they relate to different biomaterial features as well as and laryngeal tissue responses, we ranked all ellipsoids in order of decreasing volume from highest to lowest and expressed them on a scale of 100 (highest) to 1 (lowest). Data were analyzed by Kruskal-Wallis ANOVA of ranks (p=0.0004) and individual group differences compared using Mann-Whitney U test. Rank data at 4-weeks and 12-weeks after IL are shown in FIG. 5. Group 2 ellipsoid volumes were consistently larger than the three remaining groups.

In summary, MX-JC was shown to have a longer residence time in the thyroarytenoid space than either Restylane®, Cymetra®, or MX-JC co-injected with ADSCs. Specifically, it was found that MX-JC outlasts Cymetra® and Restylane® at both 4-weeks and 12-weeks post IL (i.e. Cymetra® being outperformed by over 40% and Restylane® by more than 100%).

Example 4: Histological Analysis

Materials and Methods

Figure 6:
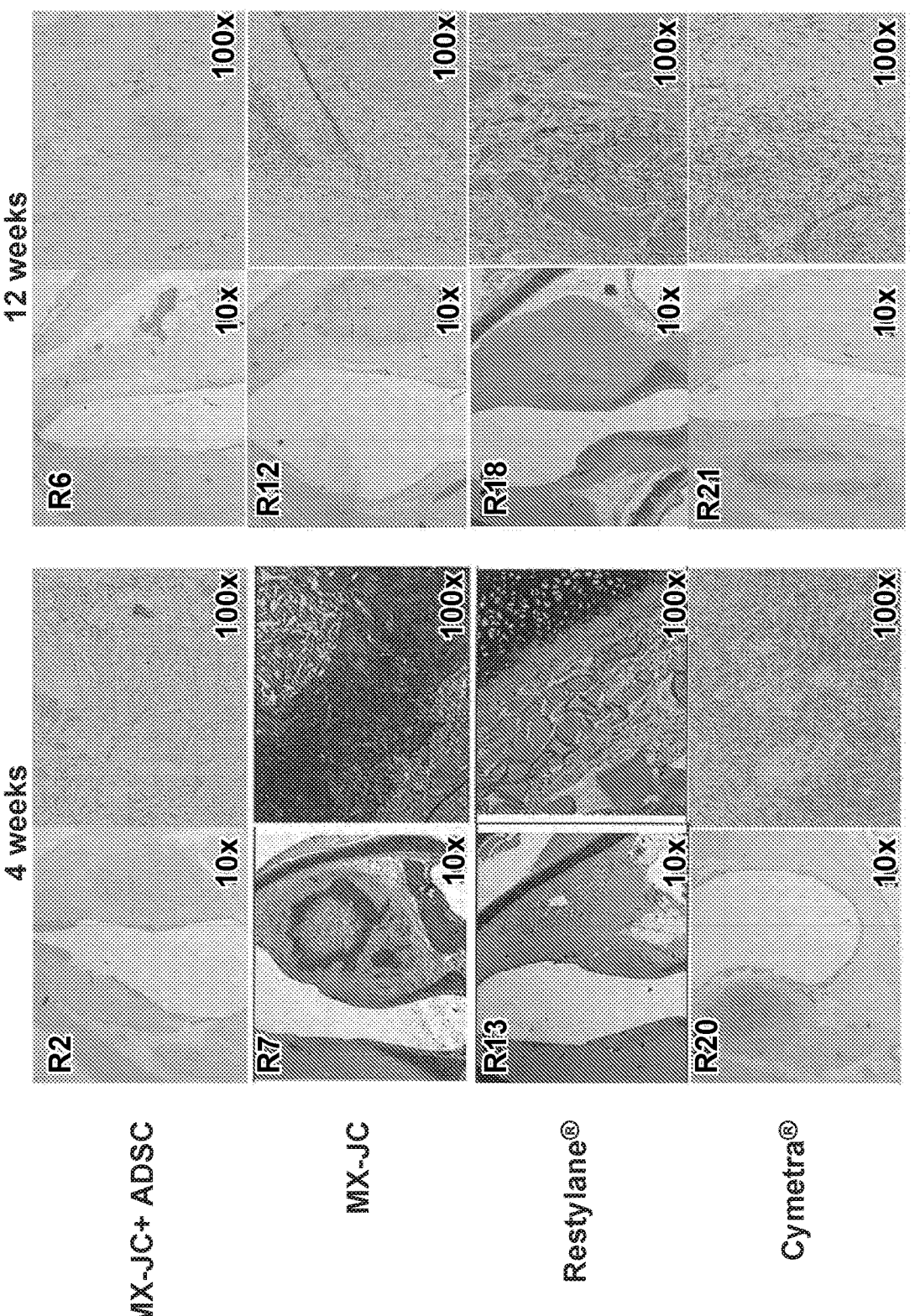
FIG. 6 shows histology analysis of tissue sections. Representative slides from each group at 4-weeks after IL and 12-weeks after IL are shown using 10× and 100× magnification (R #=rabbit number).

Histological analysis was carried out on material obtained from the animals described in Example 1. After fixation in 4% paraformaldehyde for a minimum of 72 hours, laryngeal blocks were embedded in paraffin for sectioning. Three identical size blocks were initially cut. From each block up to 72, 5 um tissue sections were laid on Corning glass slides so that all three blocks were represented on each slide. Hematoxylin and eosin staining was performed as previously described (Oldenburg et al, 2017. *Laryngoscope*, 127 (5): E166-E169; Voss et al, 2018. *Laryngoscope*, 128 (12): E402-E408). Briefly, slides were deparaffinised and stained in Harris hematoxylin solution for10 minutes then rinsed 5 minutes in running tap water. After 1-5 s. differentiation in 1% acid alcohol and 1 min rinse with tap water, bluing was performed for 3 min in 0.2% ammonia water or saturated lithium carbonate solution. Following a 5 min rinse in tap water slides and 10 dips in 95% alcohol, specimens were counterstained in eosin solution for 1 min and then dehydrated with one change of 95% ethanol, and two, 5 min changes of 100% alcohol. Finally, specimens were mounted with xylene media.
Results Representative histology data are shown in FIG. 6 and summarised in the table presented in FIG. 1.

MX-JC stained with H&E as a reticular, well-defined material surrounded by a layer of inflammatory cells. This was most apparent in Group 2 at 4 weeks post IL, whereas Group 1 was relatively free of inflammatory infiltration. By week 12, the inflammatory response in Group 2 had significantly subsided. Restylane® appeared as a bluish crystal-like material as previously reported (Zeitels et al, 2019. *Ann. Otol. Rhinol. Laryngol.*, 128(3_suppl): 71S-81S) that was easily distinguished at 4 weeks but appeared less defined at 12 weeks due to resorption. The material was relatively free of surrounding inflammatory cells. Cymetra® was similar in appearance to MX-JC, with a well-defined nodular shape that was easily visible at both 4 and 12 weeks.

In order to identify the nature of local tissue changes and inflammatory response to the injected materials slides were examined by a veterinarian pathologist, and the observations of the pathologist are summarised in the table in FIG. 1. First, some degree of muscle atrophy secondary to VF denervation was observed in all groups. Second, adipocyte infiltration was also observed in all groups and not just in Group 1, but it was not possible to distinguish injected ADSCs from proliferating local tissue adipocytes. Third, in the case of Group 3, there was widespread myocytic death and fibroplasia associated with Restylane® injections. And fourth, two distinct types of inflammatory nodules were noted with MX-JC and Cymetra®. In the case of the former, the material was surrounded by histiocytes, denoting a T cell inflammatory response while in the latter, the nodules mainly consisted of plasmocytic cells indicative of a B cell immune response.

In a previous study (Oldenburg et al, 2017. *Laryngoscope,* 127(5): E166-E169), administration of ADSCs with Cymetra® led to a predominantly lymphocytic inflammatory response. Those findings were confirmed by the results of this study (see the table in FIG. 1). It should be noted that the previously observed immunological response was of relatively equal intensity in both the Cymetra® alone group and the Cymetra®+ADSC group (Oldenburg et al, 2017. *Laryngoscope,* 127(5): E166-E169), thereby indicating that the lymphocytic inflammatory response was not muted by growth factors and cytokines secreted by ADSCs that have been traditionally associated with their immunosuppressant effect. In contrast, in the present study, MX-JC triggered a T cell-mediated immune response, characterised by dendritic cells and macrophage infiltration that was significantly downregulated by co-injection of ADSCs (compare Group 1 and Group 2 histology data in FIG. 6). The T cell-mediated response triggered in Group 2 also reduced significantly by week 12 with no obvious hallmarks of tissue destruction (except for the effects of denervation) at week 4 and at week 12 unlike that observed in Group 3.

The invention claimed is:

1. A method of treating vocal fold paralysis, wherein the method comprises administering a composition comprising jellyfish collagen to a subject in need thereof, wherein the jellyfish collagen is cross-linked.

2. The method according to claim 1, wherein the vocal fold paralysis is unilateral true vocal fold paralysis (UVFP) or bilateral vocal fold paralysis (BVFP).

3. The method according to claim 1, wherein the treatment of vocal fold paralysis is by injection medialisation laryngoplasty (IL).

4. The method according to claim 1, wherein the jellyfish collagen is in its atelo form.

5. The method according to claim 1, wherein the jellyfish collagen is in its telo form.

6. The method according to claim 1, wherein the jellyfish collagen is thiolated.

7. The method according to claim 1, wherein the jellyfish collagen is methacrylated.

8. The method according to claim 1, wherein the source of the jellyfish collagen is from the sub-phylum Scyphozoa.

9. The method according to claim 1, wherein the source of the jellyfish collagen is selected from the group consisting of: *Rhizostomas pulmo, Rhopilema esculentum, Rhopilema nomadica, Stomolophus meleagris, Aurelia* sp., *Cassiopea andromeda, Nemopilema nomurai*, or any combination thereof.

10. The method according to claim 1, wherein the jellyfish collagen is in the form of a micronised powder.

11. The method according to claim 10, wherein the micronised powder has a particle size of 1 µm to 1000 µm.

12. The method according to claim 1, wherein the jellyfish collagen is at a concentration of 1 to 500 mg/mL.

13. The method according to claim 1, wherein the composition further comprises adipose derived mesenchymal stem cells (ADSCs).

14. The method according to claim 1, wherein the composition further comprises a pharmaceutically acceptable excipient and/or carrier, and/or a pharmaceutically active ingredient.

* * * * *